United States Patent [19]

Maasbol et al.

[11] 4,267,375

[45] May 12, 1981

[54] PREPARATION OF THIOETHERS

[75] Inventors: Alfred G. Maasbol, Hamburg, Fed. Rep. of Germany; Lothar G. Dulog, St. Martens Latem, Belgium

[73] Assignee: s.a. Texaco Belgium n.v., Brussels, Belgium

[21] Appl. No.: 945,273

[22] Filed: Sep. 25, 1978

Related U.S. Application Data

[63] Continuation of Ser. No. 703,045, Jul. 6, 1976, abandoned.

[30] Foreign Application Priority Data

Nov. 19, 1975 [GB] United Kingdom ............... 47582/75

[51] Int. Cl.$^3$ ........................................... C07C 149/30
[52] U.S. Cl. ........................................ 568/57; 568/58
[58] Field of Search ........................ 260/609 E, 609 R

[56] References Cited

U.S. PATENT DOCUMENTS 2,745,878  3/1956  Mavity .............................. 260/609 E

OTHER PUBLICATIONS

I. Ruderman et al., J. Amer. Chem. Soc., 71, pp. 2264–2265, (1949).
Morrisson and Boyd, *Organic Chemistry*, 2nd edition, (1967), pp. 29–30.
T. Todsen et al., J. Amer. Chem. Soc., 72, pp. 4000–4002, (1950).
Berichte Deutsch. Chemie, vol. 1, pp. 587–591, (1935), Berlin.
D. Gregg et al., J. Org. Chem., pp. 246–252, (1950).
M. Malinovskii, *Epoxides and Their Derivatives*, pp. 131–136, (1965), Jerusalem, Daniel Davey & Co.

*Primary Examiner*—Glennon H. Hollrah
*Assistant Examiner*—M. C. Eakin
*Attorney, Agent, or Firm*—Carl G. Ries; Robert A. Kulason; Carl G. Seutter

[57] ABSTRACT

Thioethers may be prepared by reacting a thiol, such as thiophenol, with an alcohol (having electron donor groups in the alpha or beta position to its hydroxyl group) such as phenyl-1-hydroxy-phenethylsulfide. Reaction is carried out in the presence of a Lewis Acid metal halide, typically zinc chloride.

3 Claims, No Drawings

PREPARATION OF THIOETHERS

This is a continuation of application Ser. No. 703,045 filed July 6, 1976, abandoned.

Field of the Invention

This invention relates to a method for the preparation of thioethers. More particularly, this invention relates to a method for the preparation of certain thioethers by reaction between a thiol and a substituted alcohol.

DESCRIPTION OF THE PRIOR ART

Thioethers and polythioethers have been employed or suggested for employment as high temperature lubricants or as oil additives for various purposes, but their use has been hindered by the unsatisfactory methods available for their preparation.

A well known method for the preparation of thioethers is an adaptation of the Williamson synthesis involving reaction of an alkali metal derivative of a thiol with an alkyl halide.

Ruderman in J. Amer. Chem. Soc., 71, 2264 (1949) described the formation of thioethers by the reaction of thiols with "phenol alcohols." A specific example of this is the reaction between 1-butane thiol and 2-hydroxy-$\alpha^1,\alpha^3$mesitylene diol to form 2-hydroxy-$\alpha^1,\alpha^3$-bis(butylmercapto)mesitylene.

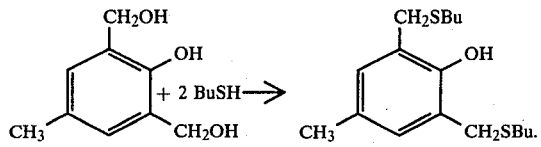

Reaction is exothermic at room temperature catalysed with hydrogen chloride or boron trifluoride.

Another method for the preparation of thioethers is described by Todsen et al. in J. Amer. Chem. Soc., 72, 4000-2 (1950). Epoxides are reacted with thiols to open the epoxide ring with formation of hydroxy groups and thioether groups on adjacent carbon atoms. This reaction is carried out in the presence of zinc chloride at elevated temperatures.

There is therefore a requirement for a method for the preparation of thioethers which is convenient and does not require complex reactants or corrosive reaction systems.

The object of the present invention is to provide a novel method for the preparation of thioethers.

SUMMARY OF THE INVENTION

The present invention provides a method for the preparation of thioethers which comprises reacting a thiol with an alcohol having an electron-donor group in the $\alpha$- or $\beta$-position to its hydroxy group in the presence of a Lewis acid metal halide as catalyst.

DESCRIPTION OF SPECIFIC EMBODIMENTS

It is essential that the alcohol used in the present invention should have an electron-donor group (nucleophilic group) in the $\alpha$ or $\beta$-position to the hydroxy group. When such groups are missing, the reaction between alcohol and thiol does not occur. For example, alkanols such as n-butanol, isobutanol or t-butanol, and unsaturated alcohols, such as allyl alcohol, have been found not to undergo reaction with thiols in the presence of Lewis acid metal halides.

When, however, an electron-donor substituent is present in the $\alpha$- or $\beta$-position to the hydroxy group, reaction with a thiol occurs readily, in some instances at room temperature, and the required thioether is obtained in large yields.

A variety of electron-donor groups can be present in the $\alpha$- or $\beta$-position to the hydroxy group of alcohols which can be employed in the method according to the present invention. For example, the electron donor group can be an ether (e.g. alkoxy) or thioether (e.g. alkylthio) group, or a substituted amino or phosphino group.

For instance, the electron-donor group can be a group of the formula $$-OR, -SR \text{ or } -PR_2$$

in which R is a substituted or unsubstituted akyl, aryl, aralkyl or alkaryl group. Alternatively it can be an aromatic or substituted aromatic group.

In general it is preferred that the electron-donor substituent should be in the $\alpha$-position rather than in the $\beta$-position since the reactivity of $\alpha$-substituted alcohols is greater than that of the $\beta$-substituted alcohols and the desired thioethers can thereby be more readily obtained, such as at lower reaction temperatures or in shorter reaction times.

According to one preferred embodiment of the invention, the electron-donor substituent can be an aromatic nucleus or substituted aromatic nucleus. A preferred class of alcohols containing such substituents has the general formula

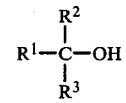

in which $R^1$ is an aromatic group or an arylmethyl group; and $R^2$ and $R^3$, which can be the same or different, are each hydrogen or an aliphatic, cycloaliphatic or aromatic hydrocarbon or substituted hydrocarbon group.

Preferably, $R^1$ is a phenyl or benzyl group, $R^2$ is hydrogen or an alkyl group and $R^3$ is hydrogen. Particularly preferred alcohols having the general formula set out above are benzyl alcohol, 1-phenethyl alcohol or 2-phenethyl alcohol.

Of the above-mentioned aralkanols, it is found that 1-phenethyl alcohol reacts with thiols more readily than benzyl alcohol and the latter compound reacts more readily with thiols than does 2-phenethyl alcohol.

According to another preferred embodiment of the invention, the electron-donor group is a thioether group, which is most preferably located on the carbon atom adjacent to the hydroxy group of the alcohol, i.e. in the $\alpha$-position.

A particularly preferred class of thioether-substituted alcohols have the formula

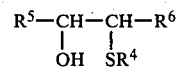

II in which $R^4$ is an aliphatic, cycloaliphatic or aromatic hydrocarbyl or substituted hydrocarbyl group; and $R^5$ and $R^6$, which may be the same or different, are each hydrogen or an aliphatic, cycloaliphatic or aromatic hydrocarbon or substituted hydrocarbon group.

In preferred compounds of the formula II, $R^4$ is an alkyl or aryl group, and one of $R^5$ and $R^6$ is hydrogen while the other is an aryl, chloromethyl or hydroxymethyl group. Such compounds may, for example, be produced by reacting an epoxide and a thiol. Such a reaction is known to involve opening of the oxirane ring of the epoxide and formation of an α-hydroxy thioether grouping. For instance, it is known from the above-mentioned paper by Todsen et al. in J. Amer. Chem. Soc., 72, 4000–2 (1950) that epichlorohydrin reacts with n-butane thiol to form 1-butylthio-3-chloropropan-2-ol.

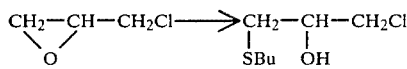

It has in fact been found that various epoxides undergo such a reaction with formation of both possible isomers. For example, it is possible to isolate both 1-butylthio-3-chloropropan-2-ol and 2-butylthio-3-chloropropan-1-ol by reacting epichlorohydrin with n-butane thiol in the presence of zinc chloride. Similar reactions are undergone by other appropriately-substituted epoxides, such as styrene oxide and glycidol.

It is accordingly possible, by employing an appropriate excess of thiol, to convert an epoxide into a vicinal bis-thioether. Suitably, the oxirano ring is opened to give a mixture of the isomeric α-hydroxy thioethers. (the proportions of which will depend upon the reactants) and the isomeric α-hydroxy thioethers then react with further thiol to form the vicinal bis-thioethers.

According to a further preferred embodiment, when a hydroxymethyl or chloromethyl substituent is adjacent to the oxirane ring, it is possible to react such a substituent with more of the thiol, with formation of a 1,2,3,-tris-thioether. For instance, epichlorohydrin and glycidol will both react with a 3-molar excess of a thiol to form propan-1,2,3-tris-thioethers.

The nature of the thiol employed in the method according to the invention is of less significance than the nature of the alcohol. The only essential is that it should not contain any substituents that interfere in the reaction according to the invention.

Preferably the thiol has the formula

in which $R^4$ is an aliphatic, cycloaliphatic or aromatic hydrocarbyl or substituted hydrocarbyl group. For example, $R^4$ can be an alkyl group, such as n-butyl or n-dodecyl, or an aromatic group, such as phenyl. Dodecyl mercaptan and phenyl mercaptan are particularly preferred thiols.

When, in the compounds of the formulae set out above, $R^1$, $R^2$, $R^3$, $R^4$, $R^5$ and $R^6$ represent substituted hydrocarbyl groups, the nature of the substituent groups is of minor significance. It is only required that they should not interfere in the reaction between the hydroxy and thiol groups in the presence of the metal halide Lewis acid catalysts.

The substituents may, for instance, themselves be hydrocarbyl groups, i.e. aliphatic hydrocarbyl groups may have aromatic substituents, forming araliphatic groups, e.g. benzyl, and aromatic hydrocarbyl groups may have aliphatic substituents, forming alkaryl groups, e.g. tolyl, or xylyl. Electron-attracting substituents should, of course, be avoided.

The catalysts used according to the invention are Lewis acid metal halides, preferably chlorides, although fluorides and bromides may also be used. A particularly preferred catalyst is zinc chloride, but other halides of polyvalent metals, such as aluminium chloride, magnesium chloride, stannous chloride, ferrous chloride, ferric chloride, antimony trifluoride, antimony pentafluoride, magnesium bromide or aluminium bromide can also be used.

The reaction temperature depends upon the nature of the reactants, the amount and nature of the catalyst, and the presence or absence of a solvent. In some instances, reaction will proceed at room temperature, while in other instances, elevated temperatures, e.g. 60° to 130° C. are preferably employed in order to provide a more rapid reaction. Where a solvent is employed, it is convenient to conduct the reaction at the reflux temperature of that solvent. The fact that temperatures as low as room temperature can be employed in some instances, is an advantage of the present invention.

The reaction according to the invention can be carried out in the presence of a solvent or in the absence of a solvent. When a solvent is used, it should, of course, be inert under the reaction conditions. Suitable solvents include, for example, hydrocarbons, especially aromatic hydrocarbons, and an especially preferred solvent is benzene, which has a convenient reflux temperature of about 80° C.

Thioethers can be employed as antioxidants, or as additives in oil compositions. Thioether alcohols are also useful as intermediates in the synthesis of detergents. For instance, they can easily be oxidised to β-hydroxyalkyl sulphoxides, which can be employed as non-ionic detergents.

The present invention is further illustrated by the following Examples:

EXAMPLE 1

1.2 g (5 m moles) of phenyl-1-hydroxyphenethylsulphide, 5 cc of thiophenol and 1 g of zinc chloride are refluxed in 10 cc of benzene for 3 hours. Evaporation and crystallization from n-hexane yield 1.28 g (70%) of 1-phenyl-1,2-bis(phenylthio)ethanae, m.p. 57° C. after recrystallization from hexane.

EXAMPLE 2

1.2 g (5 moles) of phenyl-2-hydroxyphenethylsulphide, 5 cc of thiophenol and 1 g of anhydrous zinc chloride are dissolved in 10 cc benzene and refluxed for 3 hours. After evaporation and crystallization from n-hexane 1.22 g (73%) of 1-phenyl-1,2-bis(phenylthio)ethane are obtained, m.p. 56.5°–57.5° C. after recrystallization from hexane.

EXAMPLE 3

1.5 g of anhydrous zinc chloride are dissolved in a solution of 10 cc of thiophenol in 150 cc of benzene at reflux temperature. 5 cc (43.5 m moles) of styrene oxide in 50 cc of benzene were added dropwise within one hour. After completed addition, the solvent and unreacted starting materials are removed by heating and steam distillation. The residue is extracted by ether, and the ethereal solution is dried and evaporated. A yellow oil is obtained which crystallized on standing. Recrystallization from heptane yields 8.0 g. (57%) of 1-phenyl-1,2-bis(phenylthio)ethane, m.p. 56°–57° C.

EXAMPLE 4

50 g (66.5 cc, 0.25 moles) of dodecylmercaptan, 1 g of zinc chloride and 7.7 g (6.5 cc, 0.083 moles) of epichlorohydrin are heated in an oil bath at 130° C. for seven hours, during which time gaseous hydrogen chloride is given off and water separates. After standing overnight at room temperature (about 15 hours), a white solid had formed.

Recrystallization from 1 liter of ethanol yields 43.0 g (80%) of a white solid, m.p. 35°–40° C.

From the evaporated mother liquid another portion (2.1 g) of the desired product 1,2,3-trisdodecylthiopropane is obtained by recrystallization from 150 cc of methanol-ethanol mixture (2:1). Total yield: 45.1 g (84%).

EXAMPLE 5

1 g of anhydrous zinc chloride is dissolved with warming at 50° C. in 60 g (66.5 cc, 0.25 moles) of dodecyl mercaptan. At a temperature of 50°–60° C., 12 g (10 cc, 0.12 moles) of epichlorohydrin are added dropwise. The mixture is kept at 50°–60° C. for another hour and then heated at 85°–90° C. for 20 hours. By this time 1-chloro-3-dodecylthiopropanol-2 is the only reaction product (as indicated by the infra red spectrum). The mixture is heated for five hours at 130° C., during which time water is separated and HCl gas is given off.

After 15 hours standing at room temperature overnight, a yellow oil separates and is crystallized from alcohol, yielding 38.5 g (72%) of 1,2,3-trisdodecylthiopropane. From the evaporated mother liquor, another portion of 9.0 g is obtained by recrystallization from 300 cc of methanol-ethanol mixture (2:1).

Total yield: 47.5 g (89% basis dodecylmercaptan).

EXAMPLE 6

37 g (0.5 moles) of glycidol (epoxypropanol), 101 g (0.5 moles) of dodecylmercaptan and 1 g of anhydrous zinc chloride are heated in an oil bath at 100°–120° C. for one hour.

Recrystallization of the crude product from 1.4 liters of heptane gave 3-dodecylthiopropan-1,2 diol as a white solid. Yield: 105.6 g, m.p. 53°–54° C.

0.38 g (1.3 m moles) of 3-dodecylthio-propane-1,2-diol are heated for two hours at 100° C. with an excess of dodecyl mercaptan and 0.5 g of zinc chloride.

Chromatographic separation on silica gel with benzene yields, after evapration, 0.84 g (~100%) of 1,2,3-trisdodecylthiopropane, m.p. 32°–35° C.

EXAMPLE 7

2 cc of 1-phenethylalcohol, 5 cc of thiophenol and approximately 1 g of anhydrous zinc chloride are dissolved in 30 cc of benzene and stirred at room temperature overnight (~15 hours).

Vapour phase chromatography (Vpc) indicates that the alcohol is completely disappeared and phenyl-1-phenethylsulphide is formed instead. Only minor impurities are detected by vpc and thin layer chromatography.

EXAMPLE 8

1 cc of 2-phenethylalcohol, 2.3 cc of thiophenol and 1 g of zinc chloride are dissolved in 25 cc of benzene and refluxed overnight (~20 hours). Vpc analysis indicates 20–30 percent conversion into phenyl-2-phenethylsulphide. Continued reaction did not cause much increase in yield.

EXAMPLE 9

A solution of 6.5 g (6 cc, 60 m moles) of thiophenol, 5.2 (5 cc, 48 m moles) of benzyl alcohol and 1 g of zinc chloride in 50 cc of benzene is stirred at room temperature for 20 hours. Vpc-analysis indicated no change. After refluxing for seven hours, all benzyl-alcohol had disappeared, while small amounts of thiophenol were still present and one major product had formed. The solution is extracted with aqueous acid, sodium hydroxide and water, dried over a molecular sieve and evaporated. Recrystallization yields a white solid, m.p. 38°–39° C. (80% alcohol). The comparison and mixed melting point determination with an authenic sample (38°–39° C.) indicate the identity of the product as phenyl benzyl sulphide.

Results comparable to the above (e.g. Example 1) may be attained when the following Lewis acids are used

| Example | Lewis acid |
| --- | --- |
| 10 | aluminium chloride |
| 11 | magnesium chloride |
| 12 | stannous chloride |
| 13 | ferrous chloride |
| 14 | ferric chloride |
| 15 | antimony trifluoride |
| 16 | antimony pentafluoride |
| 17 | magnesium bromide |
| 18 | aluminium bromide |

These non-limiting examples demonstrate that thioethers may be prepared in good yield under mild conditions from thiols and alcohols having electron donor groups in the alpha or beta position to their hydroxyl groups.

Obviously, many modifications and variations of our invention as hereinbefore set forth may be made without departing from the spirit and scope thereof. Therefore only such limitations should be imposed as are indicated in the following claims.

What is claimed is:

1. A method for the preparation of 1-phenyl-1,2-bis(-phenylthio)ethane wherein thiophenol is heated at reflux temperature is benzene with zinc chloride and with an oxygenated aromatic derivative selected from the group consisting of phenyl-1-hydroxyphenethyl sulphide, phenyl-2-hydroxyphenethyl sulphide and styrene oxide for a period of time sufficient to form 1-phenyl-1,2-bis(phenylthio)ethane, and 1-phenyl-1,2-bis(phenylthio)ethane is separated.

2. A method for the preparation of 1-phenyl-1,2-bis(-phenylthio)ethane which comprises heating thiophenol at reflux temperature in benzene with zinc chloride and with phenyl-1-hydroxy-phenethyl sulfide.

3. A method for the preparation of 1-phenyl-1,2-bis(-phenylthio)ethane which comprises heating thiophenol at reflux temperature in benzene with zinc chloride and with phenyl-2-hydroxy-phenethyl sulfide.

* * * * *